US011400167B2

(12) United States Patent
Michalakis et al.

(10) Patent No.: US 11,400,167 B2
(45) Date of Patent: Aug. 2, 2022

(54) GENE THERAPY FOR THE TREATMENT OF A RETINAL DEGENERATION DISEASE (71) Applicant: EyeServ GmbH, Tuebingen (DE)

(72) Inventors: Stylianos Michalakis, Munich (DE); Martin Biel, Starnberg (DE); Mathias Seeliger, Rottenburg (DE); Christian Schoen, Mittelbiberach (DE)

(73) Assignee: EYESERV GMBH, Tübingen (DE)

( * ) Notice: Subject to any disclaimer, the term of this patent is extended or adjusted under 35 U.S.C. 154(b) by 434 days.

(21) Appl. No.: 16/109,630

(22) Filed: Aug. 22, 2018

(65) Prior Publication Data

US 2018/0353620 A1 Dec. 13, 2018

Related U.S. Application Data (63) Continuation of application No. PCT/EP2017/054230, filed on Feb. 23, 2017.

(30) Foreign Application Priority Data

Feb. 23, 2016 (EP) ..................... 16156902

(51) Int. Cl.
*A61K 38/00* (2006.01)
*A61K 48/00* (2006.01)
*C12N 9/16* (2006.01)
*A61P 27/02* (2006.01)

(52) U.S. Cl.
CPC ...... *A61K 48/0058* (2013.01); *A61K 48/0066* (2013.01); *A61K 48/0075* (2013.01); *A61P 27/02* (2018.01); *C12N 9/16* (2013.01); *C12N 2750/14143* (2013.01); *C12N 2830/008* (2013.01); *C12N 2830/48* (2013.01)

(58) Field of Classification Search
CPC ............ A61K 48/0058; A61K 48/0075; A61K 48/0066; A61P 27/02; C12N 9/16; C12N 2750/14143; C12N 2830/008; C12N 2830/48
See application file for complete search history.

(56) References Cited

U.S. PATENT DOCUMENTS

| 7,186,699 B2 | 3/2007 | Harding et al. | |
|---|---|---|---|
| 8,470,790 B2 | 6/2013 | Pan et al. | |
| 10,369,231 B2 | 8/2019 | Banfi et al. | |
| 2010/0184838 A1* | 7/2010 | Kumar-Singh | .... C07K 14/4716 514/44 R |
| 2016/0022836 A1* | 1/2016 | Banfi | ................... A61K 48/005 424/450 |

FOREIGN PATENT DOCUMENTS

| JP | 2009-536219 A | 10/2009 |
|---|---|---|
| WO | WO 2005/000220 A2 | 1/2005 |
| WO | WO 2007/131180 A2 | 11/2007 |
| WO | 2012/094560 A2 | 7/2012 |
| WO | 2013/063601 A1 | 5/2013 |
| WO | 2014127196 A1 | 8/2014 |
| WO | WO 2014/140051 A1 | 9/2014 |
| WO | 2014/186160 A1 | 11/2014 |
| WO | 2015020522 A1 | 2/2015 |

OTHER PUBLICATIONS

Wert et al: "Gene therapy provides long-term visual function in a pre-clinical model of retinitis pigmentosa", (Human Molecular Genetics, vol. 22, No. 3, Oct. 29, 2012, pp. 558-567; IDS reference) (Year: 2012).*
Wert et (Human Molecular Genetics, 2014, vol. 23, No. 2, pp. 514-523, published Sep. 18, 2013). (Year: 2013).*
Wert et al., Oct. 2012, "Gene therapy provides long-term visual function in a pre-clinical model of retinitis pigmentosa", Human Molecular Genetics, vol. 22, No. 3, pp. 558-567.
Nishiguchi et al., Jan. 2015, "Gene therapy restores vision in rd1 mice after removal of a confounding mutation in Gpr179", Nature Communications, vol. 6, pp. 1-10.
Mohamed et al., Jan. 1998, "Structure and Upstream Region Characterization of the Human Gene Encoding Rod Photoreceptor cGMP Phosphodiesterase alpha-Subunit", Journal of Molecular Neuroscience, vol. 10, pp. 235-250.
Allocca et al., Oct. 2007, "Novel Adeno-Associated Virus Serotypes Efficiently Transduce Murine Photoreceptors", Journal of Virology, vol. 81, No. 20, pp. 11372-11380.
Wert et al., Sep. 2013, "Mid-stage intervention achieves similar efficacy as conventional early-stage treatment using gene therapy in a pre-clinical model of retinitis pigmentosa", Human Molecular Genetics, vol. 23, No. 2, pp. 514-523.
Sakamoto et al., Oct. 2008, "New mouse models for recessive retinitis pigmentosa caused by mutations in the Pde6a gene", Human Molecular Genetics, vol. 18, No. 1, pp. 178-192.
Corton et al., Oct. 2010, "Identification of a novel mutation in the human PDE6A gene in autosomal recessive retinitis pigmentosa: homology with the nmf28/nmf28 mice model", Clinical Genetics, vol. 78, No. 5, pp. 495-498.
Apr. 25, 2017, International Search Report and Written Opinion for International Patent Application No. PCT/EP2017/054230, 17 pages.
May 31, 2018, International Preliminary Report on Patentability for International Patent Application No. PCT/EP2017/054230, 7 pages.
Bouard et al. (2009) "Viral vectors: from virology to transgene expression," British Journal of Pharmacology, 157: 153-165.

(Continued)

*Primary Examiner* — Catherine S Hibbert
(74) *Attorney, Agent, or Firm* — Lathrop GPM LLP; James H. Velema, Esq.

(57) ABSTRACT

The present invention relates to a polynucleotide configured for the treatment of a retinal degeneration disease, such as retinitis pigmentosa (RP), a nucleic acid vector comprising said polynucleotide, a pharmaceutical composition comprising said nucleic acid vector, a kit comprising said polynucleotide or said nucleic acid vector, a method of making said nucleic acid vector, and a method for treating a retinal degeneration disease.

20 Claims, 3 Drawing Sheets

Specification includes a Sequence Listing.

(56) References Cited

OTHER PUBLICATIONS

Choi et al. (2007) "Production of Recombinant Adeno-Associated Viral Vectors for In Vitro and In Vivo Use," Current Protocols in Molecular Biology, 16.25.1-16.25.24.

Clark, K. Reed (2002) "Recent advances in recombinant adeno-associated virus vector production," Kidney International, vol. 61, Symposium 1, S9-S15.

Grieger et al. (2005) "Adeno-associated Virus as a Gene Therapy Vector: Vector Development, Production and Clinical Applications," Adv. Biochem Engin./Biotechnol., 99:119-145.

Heilbronn et al. (2010) "Viral Vectors for Gene Transfer: Current Status of Gene Therapeutics," Drug Delivery, Handbook of Experimental Pharmacology, 197:143-170.

Howarth et al. (2010) "Using viral vectors as gene transfer tools (Cell Biology and Toxicology Special Issue: ETCS-UK 1 day meeting on genetic manipulation of cells)," Cell Biol. Toxicol., 26:1-20.

Jack et al. (2015) "Predicting the Genetic Stability of Engineered DNA Sequences with the EFM Calculator," ACS Synthetic Biology, 4:939-943.

Michalakis et al. (2010) "Restoration of Cone Vision in the CNGA3−/−Mouse Model of Congenital Complete Lack of Cone Photoreceptor Function," Molecular Therapy, 18(10):2057-2063.

Zanta-Boussif et al. (2009) "Validation of a mutated PRE sequence allowing high and sustained transgene expression while abrogating WHV-X protein synthesis: application to the gene therapy of WAS," Gene Therapy, 16: 605-619.

Zolotukhin et al. (2002) "Production and Purification of serotype 1, 2, and 5 recombinant adeno-associated viral vectors," Methods, 28:158-167.

Banin et al., Sep. 2015, "Gene Augmentation Therapy Restores Retinal Function and Visual Behavior in a Sheep Model of CNGA3 Achromatopsia", Molecular Therapy, vol. 23, No. 9, pp. 1423-1433.

Biel et al. (1999) "Selective loss of cone function in mice lacking the cyclic nucleotide-gated channel CNG3," Proc. Natl. Acad. Sci. USA, 96(13):7553-7557.

Carvalho et al., May 2011, "Long-term and age-dependent restoration of visual function in a mouse model of CNGB3-associated achromatopsia following gene therapy", Human Molecular Genetics, vol. 20, No. 16, pp. 3161-3175.

Du et al., Apr. 2015, Vitreal delivery of AAV vectored Cnga3 restores cone function in Cnga3−/−/Nrl−/− mice, an all-cone model of Cnga3 achromatopsia, Human Molecular Genetics, vol. 24, No. 13, pp. 3699-3707.

Dyka et al., Jan. 2014, "Cone Specific Promoter for Use in Gene Therapy of Retinal Degenerative Diseases", Adv Exp Med Biol., vol. 801, pp. 695-701.

International Search Report and Written Opinion received for PCT Patent Application No. PCT/EP2016/053753, dated Sep. 27, 2016, 12 pages.

Komaromy et al. (2010) "Gene therapy rescues cone function in congenital achromatopsia," Human Molecular Genetics, 19(13):2581-2593.

Komaromy et al., Jul. 2008, "Targeting gene expression to cones with human cone opsin promoters in recombinant AAV", Gene Therapy, vol. 15, No. 14,, pp. 1049-1055.

Li et al. (2002) "Retinoic Acid Upregulates Cone Arrestin Expression in Retinoblastoma Cells through a Cis Element in the Distal Promoter Region," IOVS, 43(5): 1375-1383.

Pang et al. (2013) "AAV-mediated gene therapy restores cone function in the Cnga3/Nrl double knockout mouse," Invest. Ophthalmol. Vis. Sci., vol. 54, Meeting Abstract, 2 pages.

Pang et al., Apr. 2012, "AAV-Mediated Cone Rescue in a Naturally Occurring Mouse Model of CNGA3-Achromatopsia", PLOS One, vol. 7, Issue 4, pp. 1-9.

Wissinger et al. (1997) "Cloning, chromosomal localization and functional expression of the gene encoding the alpha-subunit of the cGMP-gated channel in human cone photoreceptors," European Journal of Neuroscience, 9:2512-2521.

Xiong et al in "AAV cis-regulatory sequences are correlated with ocular toxicity", PNAS, Mar. 19, 2019, vol. 116, No. 12, pp. 5785-5794.

Ye et al. (2016) "Cone-specific promoters for gene therapy of achromatopsia and other retinal diseases," Human Gene Ther., vol. 27, No. 1, pp. 72-82.

* cited by examiner

GENE THERAPY FOR THE TREATMENT OF A RETINAL DEGENERATION DISEASE

CROSS-REFERENCES TO RELATED APPLICATIONS

This application is a continuation of copending International Patent Application PCT/EP2017/054230 filed on 23 Feb. 2017 and designating the United States of America, and claims priority of European Patent Application 16 156 902.5 filed on 23 Feb. 2016, which is incorporated herein by reference.

REFERENCE TO A SEQUENCE LISTING

This application contains references to amino acid sequences and nucleic acid sequences which have been submitted concurrently herewith as the sequence listing text file "1884P101EP.txt", file size 21.1 KiloBytes (KB), created on 10 Aug. 2018. The aforementioned sequence listing is hereby incorporated by reference in its entirety pursuant to 37 C.F.R. § 1.52(e)(5).

FIELD

The present invention relates to a polynucleotide configured for the treatment of a retinal degeneration disease, such as retinitis pigmentosa (RP), a nucleic acid vector comprising said polynucleotide, a pharmaceutical composition comprising said nucleic acid vector, a kit comprising said polynucleotide or said nucleic acid vector, a method of making said nucleic acid vector, and a method for treating a retinal degeneration disease.

BACKGROUND

Retinal degeneration is the deterioration of the retina caused by the progressive and eventual death of the cells of the retina. There are several reasons for retinal degeneration, including artery or vein occlusion, diabetic retinopathy, R.L.F./R.O.P. (retrolental fibroplasia/retinopathy of prematurity), or disease (usually hereditary). These may present in many different ways such as impaired vision, night blindness, retinal detachment, light sensitivity, tunnel vision, and loss of peripheral vision to total loss of vision.

Of the retinal degenerative diseases retinitis pigmentosa (RP) is a very important example. RP denotes one of the most important types of blinding inherited eye diseases. RP is a clinically rather homogeneous but genetically heterogeneous group of disorders characterized by a primary cell death of rod photoreceptors and a subsequent secondary loss of cone photoreceptors. The disease starts in the retinal mid-periphery, and destruction progresses continuously until it reaches the retinal center and causes "tunnel vision" due to a severe circular restriction of the visual field up to legal blindness. Further clinical key features are characteristically shaped pigmentary deposits ("bone spicules") and a progressive attenuation of retinal vessels. The time course varies from early-onset forms that reach end-stage disease in childhood to late-onset forms that may retain some useful vision until advanced adulthood.

The prevalence of RP is approximately 1:4,000. RP is genetically very heterogeneous with more than 50 RP genes currently known. 10-25% of RP cases show an autosomal dominant pattern of inheritance (adRP), 6-18% are X-linked (xRP) and 20-30% are autosomal recessively inherited (arRP). Another 40-50% are sporadic and most likely represent a large fraction of arRP cases without family history. arRP is the genetically most heterogeneous RP subgroup with single genes contributing typically only a small fraction to the grand total. Most prevalent genes mutated in arRP are EYS (5-12%), USH2A (5-15%), CRB1 (~5%), and PDE6B (4-10%), but these ratios largely depend on the studied population.

PDE6A encodes the alpha subunit of the rod photoreceptor cGMP phosphodiesterase (RP43 locus). Mutations in the RP43 locus causing so-called PDE6A-linked RP or RP type 43, respectively, are found in 2-4% of arRP cases. Therefore, the absolute number of patients with PDE6A-linked arRP is approximately 900 in Germany and 5,000 in the EU.

Inherited retinal dystrophies like RP are ocular diseases caused by gene mutations. Due to the genetic nature of the disease, neither curative nor symptomatic conventional treatments have been found. The burden of disease is so severe that clinical experts put RP currently on top of their list of candidates for such therapy.

RELATED PRIOR ART

Wert et al., Gene therapy provides long-term visual function in a pre-clinical model of retinitis pigmentosa, Human Molecular Genetics 22(3). p. 558-567 (2013), also Advance Access published on 29 Oct. 2012, disclose a recombinant AAV2/8 vector comprising the mouse PDE6A gene under the control of the cell-type-specific mouse rhodopsin (RHO) promoter: AAV2/8(Y733F)-Rho-Pde6a. The retinas of mice with mutations in the gene encoding the α-subunit of PDE6, Pde6a$^{nmf363}$, were transduced with the vector. The authors state that the injection enhanced survival of photoreceptors and improved retinal function. However, according to the inventors in this approach the yield of gene replacement is not satisfactory suggesting that this strategy might be less promising for the treatment of humans suffering from retinal degenerations like in RP type 43.

SUMMARY

Against this background it is an object of the present invention to provide a polypeptide and a nucleic acid vector which address these limitations and, therefore, will be valuable tools in the treatment of a retinal degeneration disease, such as RP, in particular RP type 43.

This object is met by a polynucleotide, comprising a transgene expression cassette, comprising (a) a nucleic acid encoding the promoter of human rhodopsin gene (hRHO); (b) a nucleic acid encoding the human phosphodiesterase 6A cGMP-specific rod alpha subunit (hPDE6A) or fragments thereof, and (c) a nucleic acid encoding regulatory elements.

The inventors were able to realize that the polynucleotide of the invention embodies the essential components of a genetic tool allowing a successful therapy of a retinal degeneration disease, such as RP, which can be applied to a human patient.

It was experimentally demonstrated by the inventors that PDE6A-deficient mice which received a subretinal injection of the polynucleotide according to the invention as a component of a vector plasmid express the hPDE6A transgene efficiently and specifically in the rod photoreceptor cells. In addition, it was demonstrated that rod-mediated vision was conferred to these mice that lack rod function from birth.

This finding was surprising. It was not rendered obvious by the art that a polynucleotide having a structure as suggested by the invention would result in a targeted hPDE6A transgene expression in the retina. Therefore, the observed high specificity and selectivity as well as the significant biological effectivity of the polynucleotide of the invention in restoring the visual function were not self-evident for a person skilled in the art.

As demonstrated by the inventors in preliminary experiments after being injected into the retina the polynucleotide of the invention was specifically expressed in rod photoreceptors in a functionally active manner. Additional experiments indicate that the polynucleotide will remain in situ with only minimal transduction of off-target organs. Further experiments also indicate that after the injection into the retina of the polynucleotide of the invention no induction of anti-drug antibodies against the administered polynucleotide will occur. This allows the conclusion that the polynucleotide of the invention is well suited as an active agent of a pharmaceutical composition for the treatment of a retinal degeneration disease, such as RP.

According to the invention, a "polynucleotide" is a biopolymer molecule composed of 13 or more nucleotide monomers covalently bonded in a chain. An example of a preferred polynucleotide is a DNA molecule. While the polynucleotide according to the invention may be single-stranded or double-stranded, in a preferred embodiment the polynucleotide is single-stranded.

A "promoter" is a region of DNA that facilitates the transcription of a particular gene. As part of the process of transcription, the enzyme that synthesizes RNA, known as RNA polymerase, attaches to the DNA near a gene. Promoters contain specific DNA sequences and response elements that provide an initial binding site for RNA polymerase and for transcription factors that recruit RNA polymerase.

The promoter of the human rhodopsin gene (hRHO) refers to the region of DNA that facilitates the transcription of human rhodopsin. The entire nucleotide sequence of the promotor of hRHO is disclosed in Allocca et al., Novel adeno-associated virus serotypes efficiently transduce murine photoreceptors, Journal of Virology, 81 (2007) 11372-11380. In an embodiment the entire promotor nucleotide sequence is employed. In another embodiment of the invention only functional parts of the promotor are used which are required for a targeted expression of the hPDE6A. In still another embodiment of the invention fusions of the before mentioned nucleotide sequences with other promoter nucleotide sequences, intronic sequences or regulatory element sequences are used.

A "transgene expression cassette" or "expression cassette" comprises the gene sequences that a nucleic acid vector is to deliver to target cells. These sequences include the gene of interest (e.g., the hPDE6A nucleic acid), one or more promoters, and regulatory elements.

"Regulatory elements" are regulatory elements that are necessary for effective expression of a gene in a target cell (e.g., the hPDE6A nucleic acid), and thus should be included in a transgene expression cassette. Such sequences could include, for example, enhancer sequences, polylinker sequences facilitating the insertion of a DNA fragment within a plasmid vector, or sequences responsible for intron splicing and polyadenlyation of mRNA transcripts.

A "nucleic acid" or "nucleic acid molecule" is a molecule composed of chains of monomeric nucleotides, such as, for example, DNA molecules (e.g., cDNA or genomic DNA). A nucleic acid may encode, for example, a promoter, the hPDE6A gene or a fragment thereof, or regulatory elements. A nucleic acid molecule can be single-stranded or double-stranded.

A "nucleic acid encoding hPDE6A" refers to a nucleic acid that comprises a nucleotide sequence which codes for the human PDE6A or, in one embodiment of the invention, a fragment or a functional variant of the human PDE6A. A "fragment" of the hPDE6A refers to a segment or part of the hPDE6A which still exhibits hPDE6A activity. A "functional variant" of the hPDE6A includes a variant of the protein with minor variations such as, for example, silent mutations, single nucleotide polymorphisms, missense mutations, and other mutations or deletions, that do not significantly impair or alter the function of the wild type hPDE6A.

The amino acid sequence of hPDE6A which is encoded, at least partially, by the "nucleic acid encoding hPDE6A" according to the invention is depicted under SEQ ID No. 3.

The polynucleotide of the invention includes an "isolated" polynucleotide or nucleic acid molecule, respectively, which is one which is separated from other nucleic acid molecules which are present in the natural source of the nucleic acid. For example, with regard to genomic DNA, the term "isolated" includes nucleic acid molecules which are separated from the chromosome with which the genomic DNA is naturally associated. Preferably, an "isolated" nucleic acid molecule is free of sequences which naturally flank the nucleic acid molecule in the genomic DNA of the organism from which the nucleic acid molecule is derived.

In an embodiment of the invention said regulatory elements comprise c1) a nucleic acid encoding woodchuck stomatitis virus posttranscriptional regulatory element (WPRE).

This embodiment of the polynucleotide according to the invention has the advantage that the expression of the hPDE6A in the photoreceptor cells is significantly enhanced. The long term expression that is achieved by the inclusion of WPRE qualifies the polynucleotide for its use in gene therapy. The WPRE contains the woodchuck hepatitis virus X open reading frame (WHX ORF) gene promoter and an open-reading frame coding for the first 61 AA of WHX in its 30 region; see Zanta-Boussif et al., Validation of a mutated PRE sequence allowing high and sustained transgene expression while abrogating WHV-X protein synthesis: application to the gene therapy of WAS, Gene Ther., 16(5), 605-619 (2009).

In another embodiment of the invention in the polynucleotide according to the invention said WPRE is a mutated WPRE (WPREm), comprising a WHX OR of non-expressible WHX protein.

This measure has the advantage that it precludes the non-intended expression of the WHX protein from the expression cassette.

In another embodiment of the invention said regulatory elements comprise (c2) a nucleic acid encoding a polyadenylation signal (pA).

This measure has the advantage that the polynucleotide is provided with such a regulatory element that is important for the nuclear export, translation, and stability of the hPDE6A-encoding mRNA, thereby improving the expression efficiency.

In a further embodiment of the invention said polyadenylation signal is a bovine growth hormone pA (BGH pA).

The inventors have realized that this specific polyadenylation signal ensures especially good results when used in conjunction with the remaining genetic elements of the polynucleotide of the invention.

In another embodiment the polynucleotide of the invention further comprises a nucleic acid encoding inverted terminal repeats (ITRs) flanking said transgene expression cassette, preferably it comprises at least one ITR adjacent to said hRHO promoter (L-ITR) at the first end of the expression cassette, and at least one ITR adjacent to said pA (R-ITR) at the second end of the expression cassette opposite to the first end.

This measure has the advantage that it allows for efficient replication and packaging during manufacturing. "Flanking" means that the ITRs are located at both sides of the transgene expression cassette, i.e. at the 5' and 3' termini. The ITRs thereby frame the transgene expression cassette.

In an embodiment of the invention said ITRs are derived from Adeno-associated Virus (AAV) serotype 2 (ITR AAV2).

As it could be found this specific ITRs are particularly suited for the polynucleotide of the invention.

In another embodiment of the invention the polynucleotide comprises the following arrangement order: (a)-(b)-(c), preferably (a)-(b)-(c1)-(c2), further preferably (L-ITR)-(a)-(b)-(c1)-(c2)-(R-ITR).

The indicated order of the genetic elements has been proven as beneficial for the expression efficiency of the polynucleotide according to the invention.

In another embodiment of the invention said hRHO promoter comprises the nucleotide sequence of SEQ ID No. 1, said nucleic acid encoding hPDE6A comprises the nucleotide sequence of SEQ ID No. 2, said nucleic acid encoding hPDE6A comprises a nucleotide sequence encoding the amino acid sequence of SEQ ID No. 3, said nucleic acid encoding WPREm comprises the nucleotide sequence of SEQ ID No. 4, said nucleic acid encoding BGH pA comprises the nucleotide sequence of SEQ ID No. 5, said nucleic acid encoding L-ITR comprises the nucleotide sequence of SEQ ID No. 6 and/or said nucleic acid encoding R-ITR comprises the nucleotide sequence of SEQ ID No. 7.

This measure has the advantage that with the specific nucleotide sequences of the respective genetic elements of the polynucleotide according to the invention a precise construction manual is provided. This allows an easy and time-saving synthesis of the polynucleotide, e.g. by means of a nucleic acid synthesizer.

Another subject-matter of the invention is a nucleic acid vector comprising the above-referenced polynucleotide according to the invention. Therefore, the features, advantages and characteristics of the polynucleotide apply likewise to the nucleic acid vector of the invention.

In preferred embodiments, the nucleic acid vector according to the invention is a viral vector, such as a vector derived from an adeno-associated virus, an adenovirus, a retrovirus, a lentivirus, a vaccinia/poxvirus, or a herpesvirus (e.g., herpes simplex virus (HSV)). In the most preferred embodiments, the vector is an adeno-associated viral (AAV) vector (see below).

In an embodiment of the invention the nucleic acid vector is a circular plasmid which further comprises a backbone having a length of ≥5,000 bp, preferably ≥5.500 bp.

According to the invention, the term "backbone" refers to the section of the vector molecule beyond the expression cassette or, if present, the inverted terminal repeats (ITRs). In other words, the backbone of the vector is adjacent to the 5' and 3' termini of the expression cassette or ITRs, respectively, and forms the rest of the vector's nucleic acids besides the polynucleotide according to the invention.

The inventors have realized that a backbone of this preferred size will minimize a false or reverse packaging of the backbone into a virus particle, instead of a packaging of the expression cassette. Therefore, this measure ensures that essentially only the hPDE6A will be available for an expression in the target cell.

In another embodiment of the invention said backbone comprises ≤5 open reading frames (ORFs), preferably ≤4 ORFs, further preferably ≤3 ORFs, further preferably ≤2 ORFs, further preferably ≤1 ORFs, highly preferably ≤0 ORFs.

The inventors have realized that the backbone should be low in ORFs, preferably free in ORFs, besides any selection markers or origins of replication (ORI), if applicable. This measure has the advantage that it will further minimize the possibility for expression of side products in case of reverse packaging. In addition, it minimizes the possibility for expression of side products during manufacturing of rAAV vectors.

In still another embodiment of the nucleic acid vector according to the invention said backbone comprises a selection marker, preferably an antibiotic resistance encoding nucleic acid, further preferably a kanamycin resistance encoding nucleic acid (KanR).

This measure provides for the constructive preconditions allowing the selection of cells in vitro which incorporate the nucleic acid vector. Such cells may be used to amplify the vector.

In another embodiment of the invention said selection marker of the backbone of the nucleic acid vector is at its 5' and 3' termini remotely spaced apart from the polynucleotide, preferably maximally remotely spaced apart from the polynucleotide or expression cassette, further preferably ≥1,000 bp, further preferably ≥1,500 bp, highly preferably ≥1,900 bp spaced apart from the polynucleotide or expression cassette according to the invention.

As the inventors have realized this measure has the advantage that the resistance encoding nucleic acid (KanR) is maximally spaced apart from the ITRs and regulatory elements of the expression cassette, e.g. the promoter.

In another embodiment of the nucleic acid vector the backbone comprises ≤10 restriction enzyme recognition sites (RERSs), preferably ≤5 RERSs, further preferably ≤3 RERSs, further preferably ≤2 RERSs, further preferably ≤1 RERSs, highly preferably 0 RERSs.

This measure has the advantage that the stability of the nucleic acid vector in bacteria used for DNA amplification is significantly increased.

In another embodiment of the nucleic acid vector according to the invention the backbone comprises ≤5 promoters, preferably ≤4 promoters, further preferably ≤3 promoters, further preferably ≤2 promoters, further preferably ≤1 promoters, highly preferably 0 promoters.

This measure further minimizes the possibility for expression of side products in case of reverse packaging which may cause adverse effects or interference with the transgene. In this embodiment "promoters" are to be understood as excluding the promoter necessary for expressing the selection marker, e.g. the KanR, which will typically represented by an appropriate prokaryotic promoter.

In a further embodiment of the nucleic acid vector according to the invention said backbone further comprises an origin of replication (ORI), preferably a pUC18 ORI.

This measure provides the structural preconditions for the vector being replicable.

The backbone preferably comprises as the only encoding or information-carrying sequences the selection marker and the ORI, and for the rest random sequences but no ORFs, promoters or RERSs.

The nucleotide sequence comprised by the vector backbone is depicted in the enclosed sequence listing under SEQ ID No. 8.

In an embodiment the nucleic acid vector of the invention is an adeno-associated viral (AAV) vector.

Multiple serotypes of adeno-associated virus (AAV), including 12 human serotypes (AAV1, AAV2, AAV3, AAV4, AAV5, AAV6, AAV7, AAV8, AAV9, AAV10, AAV11, and AAV12) and more than 100 serotypes from nonhuman primates have now been identified. Howarth et al., Using viral vectors as gene transfer tools. Cell Biol. Toxicol. 26: 1-10 (2010). The serotype of the inverted terminal repeats (ITRs) or the capsid sequence of the AAV vector may be selected from any known human or nonhuman AAV serotype. In some embodiments a pseudotyping approach is employed, wherein the genome of one ITR serotype is packaged into a different serotype capsid. See e.g., Zolutuhkin et al. Production and purification of serotype 1, 2, and 5 recombinant adeno-associated viral vectors, Methods 28(2): 158-67 (2002).

While any kind of AAV could be used it is further preferred if the serotype of the AAV capsid sequence and/or the inverted terminal repeats (ITRs) of said AAV vector is selected from the group consisting of AAV2, AAV5, AAV8, or combinations thereof.

The inventors have realized that the AAV2, AAV5, AAV8 subtypes are particularly suited for the creation of the nucleic acid vector according to the invention.

The production, purification, and characterization of the recombinant AAV vectors of the present invention may be carried out using any of the many methods known in the art. For reviews of laboratory-scale production methods, see, e.g., Clark, Recent advances in recombinant adeno-associated virus vector production. Kidney Int. 61s:9-15 (2002); Choi et al., Production of recombinant adeno-associated viral vectors for in vitro and in vivo use. Current Protocols in Molecular Biology 16.25.1-16.25.24 (2007); Grieger and Samulski, Adeno-associated virus as a gene therapy vector: Vector development, production, and clinical applications. Adv. Biochem. Engin/Biotechnol 99: 119-145 (2005); Heilbronn and Weger, Viral Vectors for Gene Transfer: Current Status of Gene Therapeutics, in M. Schafer-Korting (Ed.), Drug Delivery, Handbook of Experimental Pharmacology, 197: 143-170 (2010); Howarth et al. (l.c.). The production methods described below are intended as non-limiting examples.

Another subject-matter of the invention is a pharmaceutical preparation comprising the nucleic acid vector as described in detail further above, and a pharmaceutically acceptable carrier. Therefore, the features, advantages and characteristics of the polynucleotide and the nucleic acid vector apply likewise to the pharmaceutical preparation of the invention.

Pharmaceutically acceptable carriers are well known in the art. By way of example, reference is made to Rowe (Ed.) (2012), Handbook of Pharmaceutical Excipients, 6$^{th}$ Edition, Pharmaceutical Press. The pharmaceutical preparation may further contain additives. These include any compound or composition which are advantageous for the effectiveness of the nucleic acid vector according to the invention, such as salts, binders, solvents, dispersants, adjuvants and other substances commonly used in connection in gene therapeutic approaches.

In an embodiment of the pharmaceutical preparation said pharmaceutically acceptable carrier comprises saline solution, preferably balanced sterile saline solution, and optionally a surfactant, preferably micronized poloxamer (Kolliphor® P 188 micro).

The inventors have realized that with such specific formulation drug induced adverse effects and loss of rAAV particles at surfaces are minimized.

In an embodiment the pharmaceutical preparation according to the invention is configured for a use in the treatment of a disease associated with a genetic mutation, substitution, or deletion that affects retinal degeneration, preferably for the treatment of an inherited retinal dystrophy, further preferably of retinitis pigmentosa (RP), and highly preferably RP type 43 (RP43).

With the polynucleotide and the nucleic acid vector described in detail further above the inventors provide a therapeutic tool which, for the first time, allows a causative treatment of PDE6A-linked RP.

Another subject-matter of the present invention is a kit comprising (a) the polynucleotide according to the invention and/or the nucleic acid according to the invention, and/or the pharmaceutical preparation according to the invention, and (b) instructions for use thereof.

A further subject-matter of the present invention is a method of making a recombinant adeno-associated viral (rAAV) vector comprising inserting into an adeno-associated viral vector the polynucleotide according to the invention, preferably said recombinant adeno-associated viral vector is the nucleic acid vector according to the invention.

Another subject-matter of the invention is a method for treating a disease associated with a genetic mutation, substitution, or deletion that affects retinal degeneration, wherein the method comprises administering to a subject in need of such treatment the nucleic acid vector according to the invention and/or the pharmaceutical preparation according to the invention, thereby treating the subject. Preferably the disease is inherited retinal dystrophy, further preferably retinitis pigmentosa (RP), and highly preferably RP type 43 (RP43). Preferably the vector is administered subretinally and/or intravitreally.

The features, advantages and characteristics of the polynucleotide and the nucleic acid vector apply likewise to the kit, the method of making and the method for treating according to the invention.

It is to be understood that the before-mentioned features and those to be mentioned in the following cannot only be used in the combination indicated in the respective case, but also in other combinations or in an isolated manner without departing from the scope of the invention.

The invention is now further explained by means of embodiments resulting in additional features, characteristics and advantages of the invention. The embodiments are of pure illustrative nature and do not limit the scope or range of the invention. The features mentioned in the specific embodiments are general features of the invention which are not only applicable in the specific embodiment but also in an isolated manner in the context of any embodiment of the invention.

The invention is now described and explained in further detail by referring to the following figures and non-limiting examples.

EXAMPLES

1. Nucleic Acid Vector of the Invention

Figure 1:
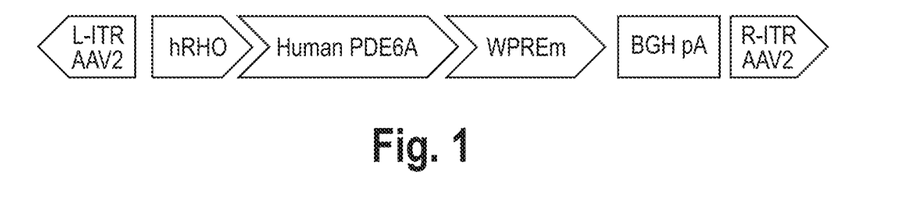
FIG. 1 shows the structure of the rAAV.hPDE6A vector genome.

In this exemplary embodiment the rAAV.hPDE6A vector is a hybrid AAV-based vector carrying the cDNA of the human hPDE6A subunit of the rod photoreceptor cGMP phosphodiesterase. The hPDE6A cDNA expression is under the control of the rod-specific Rhodopsin promoter (hRHO) and is enhanced using a mutated woodchuck stomatitis virus posttranscriptional regulatory element (WPRE) sequence. The expression cassette is flanked by the AAV serotype 2 inverted terminal repeats (ITRs) and the recombinant genome is packaged in the AAV serotype 8 capsid. The expression cassette comprises the following elements:

Promoter of the human rhodopsin gene: 0.8 Kb
cDNA of the human PDE6A subunit of the rod photoreceptor cGMP phosphodiesterase: 2.58 Kb
Woodchuck stomatitis virus posttranscriptional regulatory element (WPRE) with a point mutation in the ATG codon of the WHV-X open reading frame: 0.54 Kb
Polyadenylation signal of the Bovine Growth Hormone (BGH): 0.2 Kb
AAV serotype 2 inverted terminal repeats (ITRs): 0.13 Kb The structure of the rAAV.hPDE6A vector genome is depicted in FIG. 1.

2. phRHO.hPDE6A.WPREm cis Vector Plasmid

In one exemplary embodiment the phRHO.hPDE6A.WPREm cis vector plasmid backbone is used that contains an expression cassette comprising a 806 bp rod photoreceptor-specific human rhodopsin (hRHO) promoter [see Allocca et al., Novel adeno-associated virus serotypes efficiently transduce murine photoreceptors, Journal of Virology, 81 (2007) 11372-11380] and the full-length (2579 bp) human PDE6A cDNA. The expression cassette also contains a 543 bp woodchuck hepatitis virus posttranscriptional regulatory element (WPRE) with mutated WXF-open reading frame [Zanta-Boussifet al., Validation of a mutated PRE sequence allowing high and sustained transgene expression while abrogating WHV-X protein synthesis: application to the gene therapy of WAS, Gene therapy, 16 (2009), 605-619] and a 207 bp bovine growth hormone polyadenylation signal (BGHpA). The 5591 bp vector backbone with the nucleotide sequence depicted in SEQ ID No. 8 containing a kanamycin resistance (KanR) positioned 1943 bp from the L-ITR and 2853 bp from the R-ITR and 2024 bp from a pUC18 ori.

The rAAV.hPDE6A vector is produced using transient double-transfection of the cis vector plasmid and a trans pDP8-KanR helper plasmid in the human embryonic kidney 293 cells (HEK293). The cell lysate is clarified by a low-speed centrifugation and the vector is then purified by 2 consecutive rounds of cesium chloride gradients ultracentrifugation followed by a tangential flow filtration step for concentration and buffer exchange. The resulting rAAV.hPDE6A vector suspension is then sterile-filtered and vialed as drug product.

Figure 2A:
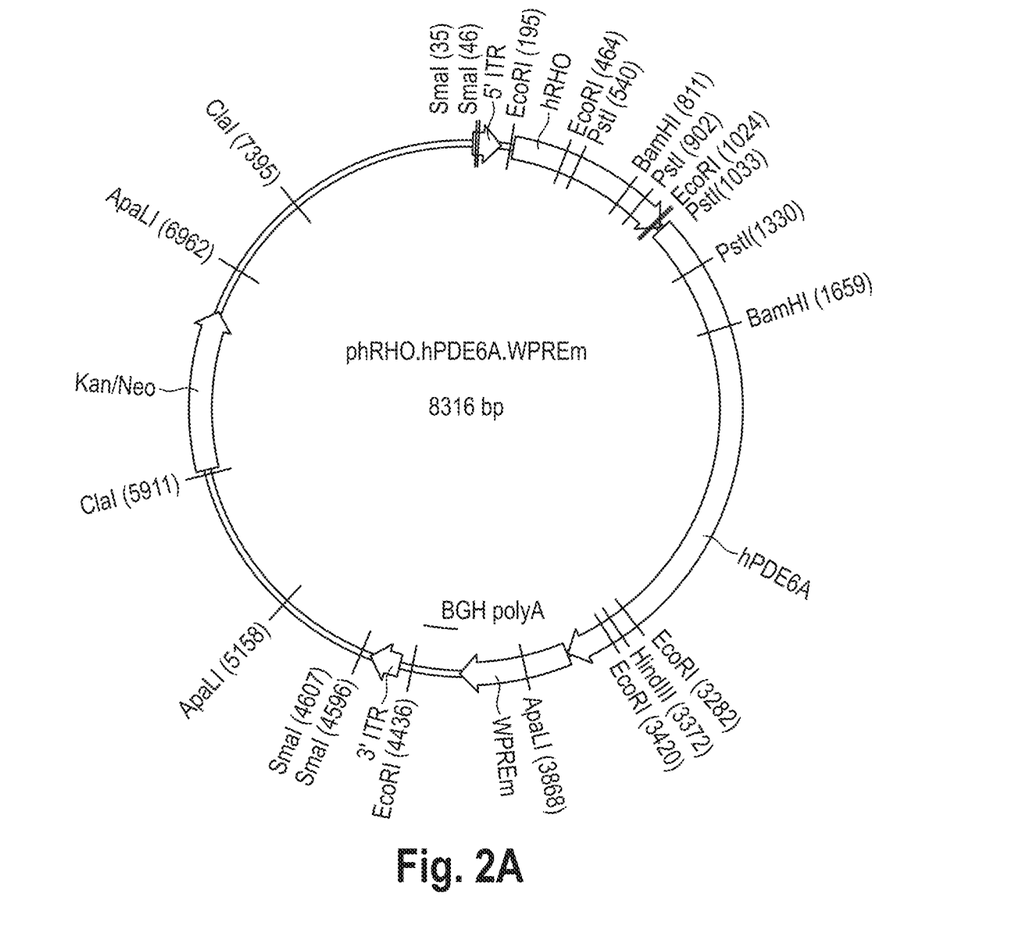
FIGS. 2A-2B show two embodiments of the phRHO.hPDE6A.WPREm cis vector plasmid map.
Figure 2B:
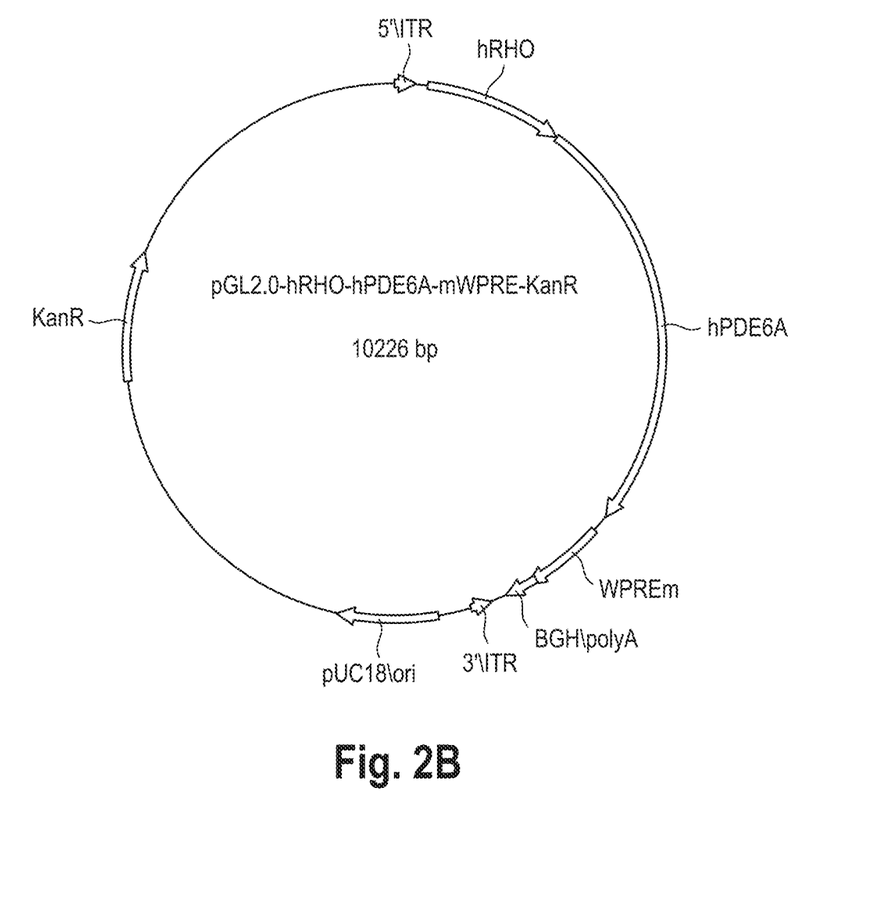

Two embodiments of the phRHO.hPDE6A.WPREm cis vector plasmid map are shown in FIGS. 2A, B.

3. Biological Activity and Transgene Expression Conferred by the rAAV.hPDE6A

To verify biological activity and transgene expression the inventors delivered the rAAV.hPDE6A vector into the subretinal space of 2-week-old PDE6A D670G mutant mice [see Sakamoto et al., New mouse models for recessive retinitis pigmentosa caused by mutations in the Pde6a gene, Hum Mol Genet, 18 (2009) 178-192]. The delivery procedure was similar to the one described in Michalakis et al., Restoration of cone vision in the CNGA3−/− mouse model of congenital complete lack of cone photoreceptor function, Molecular therapy: The Journal of the American Society of Gene Therapy, 18 2057-2063 (2010). The mice received a subretinal injection in the treated eye (TE), whereas the other, untreated eye (UE) served as control. The vector efficacy was evaluated at 3 weeks following the injection by means of electroretinography (ERG), an objective functional in vivo assay. PDE6A D670G mutant mice lack normal rod photoreceptor function. Secondary to rods, non-affected cone photoreceptors also degenerate resulting in loss of cone function at later stages of the disease. Therefore, ERG protocols specifically testing for rod and cone function are suitable as an indirect measure for PDE6A function and for the assessment of biological activity (BAA) of the rAAV.hPDE6A vector.

Figure 3:
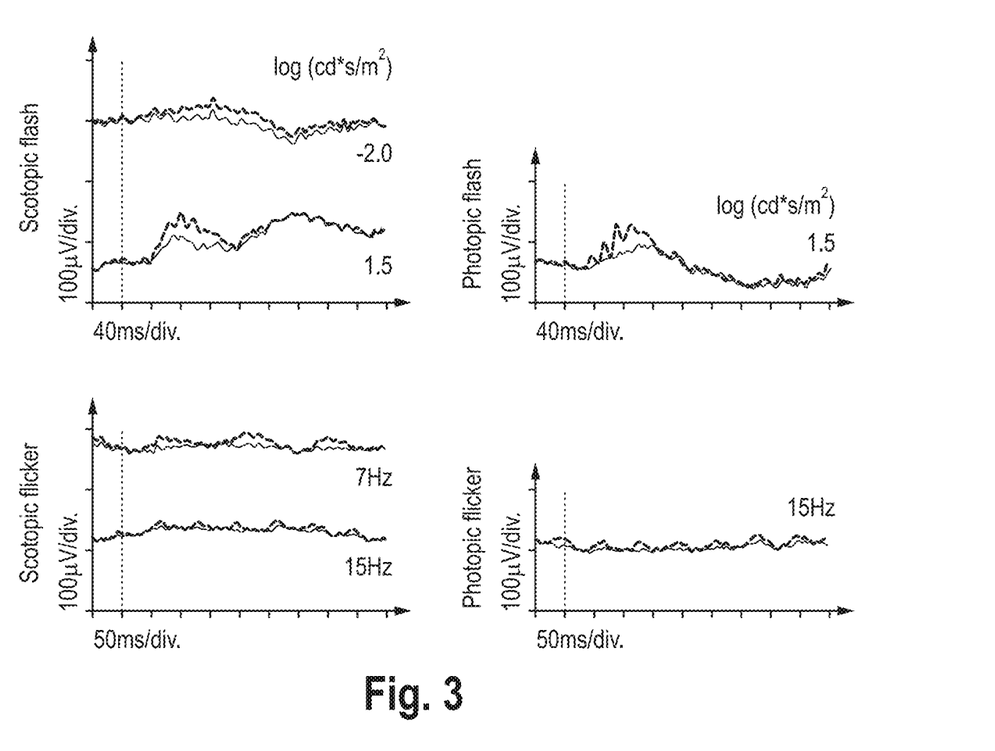
FIG. 3 shows representative ERG measurements from PDE6A D670G mutant mice treated on one eye with the vector according to the invention.
Figure 4A:
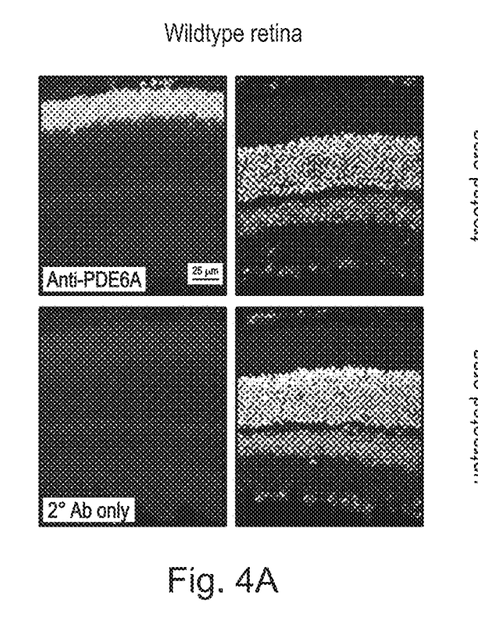
FIGS. 4A-4B depict representative confocal images from immunohistological stainings of hPDE6A in PDE6A D670G mutant mice treated with the vector according to the invention.
Figure 4B:
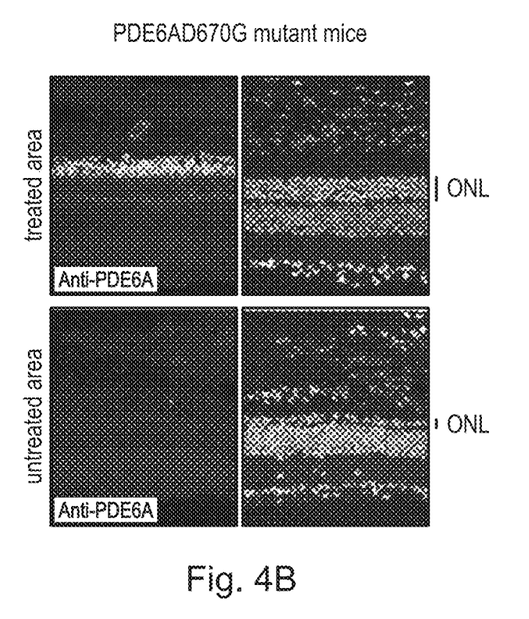

For representative results see FIG. 3. The rAAV.hPDE6A vector treatment resulted in a clear therapeutic effect in the treated eye reflected by a distinct side difference of specific ERG component amplitudes between treated and untreated eyes. After completion of the ERG measurements mice were sacrificed, the eyes enucleated and processed for immunohistological analysis of hPDE6A transgene expression (transgene expression assay, TEA). For this, the tissue was fixed and cryoembedded. Vertical cryosections were stained with a rabbit polyclonal antibody (anti-PDE6A, #NBP1-87312, Novus, Littleton, Colo.) directed against human PDE6A protein. The immunosignal was detected with an Alexa 488 tagged donkey anti-rabbit IgG secondary antibody. Confocal images from the immunostained cryosections were collected using a Leica SP8 SMD confocal laser scanning microscope. The anti-PDE6A antibody also detects mouse Pde6a protein and gives a specific signal in rod photoreceptor outer segments of wildtype mouse retina and no signal in Pde6a-deficient (PDE6A D670G mutant) retina. After treatment with rAAV.hPDE6A vector a clear and specific signal for PDE6A was observed in rod photoreceptors in the treated eye, which was absent in the untreated eye; see FIG. 4. Staining of the retinal cryosections with the nuclear dye Hoechst 3442 also revealed a beneficial effect of the treatment on retinal degeneration, which was evident as substantial preservation of the outer nuclear layer of the retina in the treated eye compared to the untreated eye.

For representative results see FIG. 4: Representative confocal images from immunohistological stainings of hPDE6A (light grey) in PDE6A D670G mutant mice treated with rAAV.hPDE6A vector. The antibody (anti-PDE6A, working dilution in all experiments 1:500) also detects mouse PDE6A protein and gives a specific signal in rod photoreceptor outer segments (strongly stained structures in the upper part of the image) of wildtype mouse retina (A, upper panel) and no specific signal in the retina of untreated PDE6A D670G mutant mice (B, lower panel). The specific signal for the hPDE6A protein encoded by the rAAV.hPDE6A vector is shown in (B, upper panel). The lower panel in (A) shows a secondary antibody only control staining. The retinal cross-sections were also stained with Hoechst 3442 dye to visualize the retinal cell nuclei (grey signal). The rAAV.hPDE6A-mediated expression of hPDE6A clearly delayed rod photoreceptor degeneration in the PDE6A D670G mutant retina: compare outer nuclear layer (ONL) thickness between upper (treated eye) and lower (untreated eye) in (B).

In conclusion, the rAAV.hPDE6A vector expresses the hPDE6A transgene efficiently and specifically in rod photoreceptors of PDE6A D670G mutant mice, which substantially delays photoreceptor degeneration in treated areas. Importantly, the prolonged survival of rods counteracts the 'bystander effect', which leads to a loss of cones-independent from the underlying disease in all areas where rods are lost. The biological activity data illustrate the extended preservation of cone-mediated vision in these mice, which is of particular significance for applications of the treatment in respective forms of human retinitis pigmentosa.

4. AAV8 Biodistribution and Shedding After Subretinal Injection in Non-Human Primates In another study 21 Cynomolgous monkeys received subretinal injections in three cohorts (high dose: $1 \times 10^{12}$ vector genomes [vg], low dose: $1 \times 10^{11}$ vg, or vehicle only). The virus distribution and shedding was analysed after a single subretinal administration of clinical grade recombinant adeno-associated virus (rAAV) in non-human primates. This is important for an environmental risk assessment of the gene therapeutic method according to the invention.

Tissues samples were harvested at necropsy (day 91) from the treated eye, draining lymph nodes, salivary gland and spleen, optic nerve, brain and spinal cord, heart, lung, liver, adrenal glands and gonads. Blood, urine, lacrimal and nasal swabs were harvested from each animal prior to dosing and 1, 2 and 3 days and 1, 4 and 13 weeks after application of the vector for DNA extraction and quantification of vector genomes by qPCR.

Dose dependent rAAV DNA was found in the treated retina. Quantifiable levels of rAAV DNA were also detected in the optic nerve of 2 animals of the low dose and 3 animals of the high dose group. Transient shedding of rAAV DNA was found in nasal and lachrymal fluids and urine. rAAV DNA was not detected in the germ line tissues and apart from sporadic signals detected in a small number of animals in lymph nodes and spleen, all remaining tissues were negative or showed levels which were below the limit of quantification. Blood samples were negative or showed non-quantifiable levels at all time points tested.

These data are relevant for the clinical implementation of the invention, where trial subjects, investigators and regulators alike are interested to identify environmental risks associated with application of genetically modified organisms. While shedding into biofluids seems to occur in a dose dependent manner, transduction of off-target organs seems minimal.

5. Humoral Immune Response to Subretinal AAV8 in Non-Human Primates

Knowledge of the humoral immune response to single subretinal administration of clinical grade recombinant adeno-associated virus (rAAV) in non-human primates is a key factor for the development of safe and efficient clinical trial protocols for the retinal gene therapy according to the invention. For this reason the inventors explored anti-drug-antibody (ADA) titres in non-human primates (*Macacca fascicularis*) after single subretinal administration of a rAAV8-pseudotyped virus.

21 monkeys received subretinal injections in three cohorts (high dose: $1 \times 10^{12}$ vector genomes [vg], low dose: $1 \times 10^{11}$ vg, or vehicle only) and concomitant immunosuppressive therapy equivalent to a clinical trial scenario. Baseline samples were compared to those taken 1, 2 and 3 days and 1, 4 and 13 weeks after application of the vector.

This study provides data relevant for a clinical application of the invention, where rAAV8 might be used for subretinal delivery of the hPDE6A transgene. When mimicking the clinical scenario with clinical grade vector, surgery and concomitant immunosuppression, no induction of anti-drug-antibodies occurred in non-human primates.

6. Toxicity

Assessment of toxicity was based on evaluation of clinical observations, body weights, ophthalmic fundus and slit lamp (SLO) examinations, macroscopic examinations, fundus photography, optical coherence tomography (OCT)—(including indocyaningreen angiography and fluorescence angiography [FA]), intraocular pressure (IOP), electroretinography (ERG), organ weights, and on macroscopic and microscopic assessments.

No test item-related mortalities or clinical observations were noted.

No adverse or test item-related findings were noted on body weights, ECGs, blood pressure, clinical pathology, urinalysis, or immunoglobulin evaluation.

No test item-related changes were noted during ophthalmic assessments. The IOP (transient increases), ERG (increased implicit times), OCT (shortening of photoreceptor outer segments), SLO (clumping of the retinal pigment epithelium [RPE], atrophy of the RPE or choroid, leakage in the FLA), and funduscopy (hyper- and hypo-pigmentation) findings were procedure related because they also occurred in control monkeys.

Very subtle structural procedure-related (i.e., caused by the subretinal injection) changes occurred in the outer retina (photoreceptor outer segments [POS]). These changes consisted of a shortening of the POS, a structure that is undergoing constant recycling/renewal (10% each day). The POS are known to be shortened for up to 6 months after subretinal surgery (Schaffer et al., 1993).

No findings were noted on organ weights or macroscopic observations.

In conclusion, subretinal administration of rAAV.hPDE6A was well tolerated up to the highest dose of 1×10E12 vg in male and female cynomolgus monkeys. The only test item-related change was minimal retinal transient perivascular inflammation, which was likely associated with the rAAV vector. Minimal disturbances in the RPE were found in all groups, including controls, and were procedure related.

7. Nucleic Acid Sequences

The following nucleotide and amino acid sequences are identified in the sequence listing.

hRHO promoter nucleotide sequence: SEQ ID No. 1 hPDE6A nucleotide sequence: SEQ ID No. 2 hPDE6A amino acid sequence: SEQ ID No. 3

WPREm nucleotide sequence: SEQ ID No. 4

BGH pA nucleotide sequence: SEQ ID No. 5

L-ITR nucleotide sequence: SEQ ID No. 6

R-ITR nucleotide sequence: SEQ ID No. 7

What is claimed is:

1. A nucleic acid adeno-associated virus (AAV) vector comprising a polynucleotide, said polynucleotide comprising
   a transgene expression cassette, comprising
   (a) a nucleic acid comprising the promoter of human rhodopsin gene (hRHO);
   (b) a nucleic acid encoding the human phosphodiesterase 6A cGMP-specific rod alpha subunit (hPDE6A) or encoding fragments thereof exhibiting hPDE6A activity, and
   (c) a nucleic acid encoding regulatory elements necessary for expression of hPDE6A,
   wherein said nucleic acid vector is a circular plasmid further comprising a back-bone having a length of at least 5,000 bp, and
   wherein said regulatory elements comprise
   (c1) a woodchuck stomatitis virus posttranscriptional regulatory element (WPRE) comprising the nucleotide sequence of SEQ ID NO: 4.

2. The nucleic acid vector of claim 1, wherein said regulatory elements comprise
   (c2) a polyadenylation signal (pA).

3. The nucleic acid vector of claim 2, wherein said polyadenylation signal is a bovine growth hormone pA (BGH pA) comprising the nucleotide sequence of SEQ ID NO: 5.

4. The nucleic acid vector of claim 1, wherein it further comprises a nucleic acid encoding inverted terminal repeats (ITRs) flanking said transgene expression cassette.

5. The nucleic acid vector of claim 4, wherein said ITR comprises an L-ITR comprising the nucleotide sequence of SEQ ID NO: 6.

6. The nucleic acid vector of claim 4, wherein said ITR comprises an R-ITR comprising the nucleotide sequence of SEQ ID NO: 7.

7. The nucleic acid vector of claim 1 comprising an arrangement order selected from the group consisting of:
   (a)-(b) (c), (a)-(b) (c1)-(c2), and (L-ITR)-(a)-(b)-(c1)-(c2)-(R-ITR),
   wherein (c1) comprises a nucleic acid encoding a woodchuck stomatitis virus posttranscriptional regulatory element (WPRE),
   wherein (c2) comprises a nucleic acid encoding a polyadenylation signal (pA),
   wherein (ITR) comprises a nucleic acid encoding inverted terminal repeats (ITRs) flanking said transgene expression cassette,
   wherein at least one ITR is adjacent to said hRHO promoter (L-ITR) and at least one ITR is adjacent to said pA (R-ITR).

8. The nucleic acid vector of claim 1, wherein said hRHO promoter comprises the nucleotide sequence of SEQ ID NO:1.

9. The nucleic acid vector of claim 1, wherein said backbone comprises a length of 5,500 bp.

10. The nucleic acid vector of claim 1, wherein said backbone comprises
    up to 5 open reading frames (ORFs) or
    a selection marker, or
    up to 10 restriction enzyme recognition sites (RERSs), or
    up to 5 promoters, or
    an origin of replication (ORI), or
    a combination thereof.

11. The nucleic acid vector of claim 1, wherein said backbone comprises the nucleotide sequence of SEQ ID No. 8.

12. The nucleic acid vector of claim 1, wherein the vector is an adeno-associated viral (AAV) vector.

13. A pharmaceutical preparation comprising the nucleic acid vector of claim 1.

14. A method of treating of a disease associated with a genetic mutation, substitution, or deletion that affects retinal degeneration comprising administering the pharmaceutical composition of claim 13.

15. A method for treating a disease associated with a genetic mutation that affects retinal degeneration, wherein said method comprises administering to a subject in need of such treatment the pharmaceutical composition of claim 13, thereby treating the subject.

16. The nucleic acid vector of claim 1, wherein said hPDE6A comprises the nucleotide sequence of SEQ ID NO: 2.

17. A method for treating a disease associated with a genetic mutation that affects retinal degeneration, wherein said method comprises administering to a subject in need of such treatment the nucleic acid vector of claim 1, thereby treating the subject.

18. The method of claim 17, wherein the disease is selected from the group consisting of: inherited retinal dystrophy, retinitis pigmentosa (RP), and RP type 43 (RP43).

19. The method of claim 17, wherein the vector is administered subretinally or intravitreally.

20. A kit comprising
   (a) the nucleic acid vector of claim 1, and
   (b) instructions for use thereof.

* * * * *

SEQUENCE LISTING

<160> NUMBER OF SEQ ID NOS: 8

<210> SEQ ID NO 1
<211> LENGTH: 848
<212> TYPE: DNA
<213> ORGANISM: Artificial Sequence
<220> FEATURE:
<223> OTHER INFORMATION: hRHO promoter nucleotide sequence

<400> SEQUENCE: 1

| | | | | |
|---|---|---|---|---|
| gctagcagat | cttccccacc | tagccacctg | gcaaactgct | ccttctctca aaggcccaaa | 60 |
| catggcctcc | cagactgcaa | ccccaggca | gtcaggccct | gtctccacaa cctcacagcc | 120 |
| accctggacg | gaatctgctt | cttcccacat | ttgagtcctc | ctcagcccct gagctcctct | 180 |
| gggcagggct | gtttctttcc | atctttgtat | tcccaggggc | ctgcaaataa atgtttaatg | 240 |
| aacgaacaag | agagtgaatt | ccaattccat | gcaacaagga | ttgggctcct gggccctagg | 300 |
| ctatgtgtct | ggcaccagaa | acggaagctg | caggttgcag | ccctgccct catggagctc | 360 |
| ctcctgtcag | aggagtgtgg | ggactggatg | actccagagg | taacttgtgg gggaacgaac | 420 |
| aggtaagggg | ctgtgtgacg | agatgagaga | ctgggagaat | aaaccagaaa gtctctagct | 480 |
| gtccagagga | catagcacag | aggcccatgg | tccctatttc | aaacccaggc caccagactg | 540 |
| agctgggacc | ttgggacaga | caagtcatgc | agaagttagg | ggaccttctc ctcccttttc | 600 |
| ctggatcctg | agtacctctc | ctccctgacc | tcaggcttcc | tcctagtgtc accttggccc | 660 |
| ctcttagaag | ccaattaggc | cctcagtttc | tgcagcgggg | attaatatga ttatgaacac | 720 |
| ccccaatctc | ccagatgctg | attcagccag | gagcttagga | gggggaggtc actttataag | 780 |
| ggtctggggg | ggtcagaacc | cagagtcatc | cgcctgaatt | ctgcagatat ccatcacact | 840 |
| ggcggccg | | | | | 848 |

<210> SEQ ID NO 2
<211> LENGTH: 2581
<212> TYPE: DNA
<213> ORGANISM: Artificial Sequence
<220> FEATURE:
<223> OTHER INFORMATION: hPDE6A nucleotide sequence

<400> SEQUENCE: 2

| | | | | |
|---|---|---|---|---|
| atgggcgagg | tgacagcaga | ggaggtggag | aagttcctgg | actcgaatat tggctttgcc | 60 |
| aaacagtact | acaacctcca | ctaccgggcc | aagctcatct | ccgacctcct tggggccaag | 120 |
| gaggctgccg | tggacttcag | caactaccac | tccccgagca | gcatggagga gagcgaaatc | 180 |
| atctttgatc | tcctgcggga | ctttcaggag | aatttacaga | cagagaaatg catcttcaat | 240 |
| gtcatgaaga | agctgtgctt | cctcctgcag | gcagaccgca | tgagcctgtt catgtaccgg | 300 |
| acccgcaatg | gcatcgcaga | gctggccacc | aggcttttca | atgtccacaa ggatgctgtc | 360 |
| ctcgaggact | gcctggtgat | gcccgaccaa | gagatcgtct | tccctttgga catgggcatc | 420 |
| gtgggccatg | tcgcacactc | taagaaaatt | gctaacgtcc | ccaacacaga ggaggatgag | 480 |
| catttctgtg | actttgtgga | catcctcaca | gagtacaaga | ccaagaacat cttggcttcc | 540 |
| cccataatga | tgggaaggga | tgtggtggcc | ataatcatgg | ctgtgaataa agtggatgga | 600 |
| tcccacttca | ccaagagaga | tgaagagatt | ctctcaagt | acctcaattt tgcaaatcta | 660 |
| atcatgaagg | tgtaccacct | gagttacctg | cacaactgtg | aaactcgacg tggccagata | 720 |
| ctgctgtggt | ctgggagcaa | agtctttgaa | gaacttacgg | acatcgaacg acagttccac | 780 |
| aaagccctgt | acacagtccg | tgctttcctc | aactgtgaca | gatactctgt gggtctctta | 840 |

```
gacatgacca agcagaagga attttttgat gtgtggccgg ttctgatggg tgaagttcca      900
ccttactctg gtcccaggac tccggatgga agagaaatta acttttacaa ggtcattgac      960
tacatcctgc atggcaaaga ggacatcaaa gtcatcccga atccacctcc tgaccattgg     1020
gctttagtaa gcggtctccc agcttatgtt gcccagaatg gcctgatttg caacatcatg     1080
aatgcgcctg cggaggactt ttttgcattt cagaaagaac tctggatga gtctggatgg      1140 atgattaaaa atgtgctttc aatgccgatt gtgaacaaga aggaagaaat tgttggagtg     1200
gccacatttt acaatcgtaa agatgggaag ccctttgatg aaatggatga acgctcatg      1260 gagtctttga ctcaatttct gggctggtct gtcttaaatc ctgacaccta tgagtcaatg     1320
aataaacttg aaaataggaa ggatattttc caggacatag taaaatatca tgtgaagtgt     1380
gacaatgaag aaattcagaa aatcttgaaa accagagagg tgtatgggaa ggagccatgg     1440
gagtgtgagg aagaggagct ggctgagatc ctgcaagcgg agctgccaga tgcagataaa     1500
tacgaaatta ataaatttca cttcagtgac ttaccectaa cagaactgga gctggtaaaa     1560
tgtggaatac agatgtatta tgagctcaaa gtggtggata aatttcacat tccacaagag     1620
gccctggtgc ggttcatgta ctccctgagt aagggctacc gcaagatcac ctaccacaac     1680
tggcggcacg gcttcaacgt ggggcagacc atgttctccc tgctggtgac gggaaagctg     1740
aagcgctact tcacggacct agaggccttg gccatggtca ctgctgcttt ctgccatgac     1800
attgaccaca gaggcaccaa taacctctac cagatgaaat cccagaaccc actggccaag     1860
ctccatgggt cctctatctt ggaaagacac cacttggagt ttggcaaaac actgctcaga     1920
gacgagagcc tgaatatctt tcaaaacctc aatcgtcgac agcatgagca tgccatccac     1980
atgatggaca ttgcaatcat tgccacagac ctcgccctgt atttcaagaa gaggacgatg     2040
ttccaaaaga tcgtggatca gtctaagaca tatgagagtg aacaggagtg gacacagtac     2100
atgatgctgg agcagacacg gaaggaaatc gttatggcca tgatgatgac cgcctgtgat     2160
ctctcagcca tcaccaaacc ctgggaggtg cagagccagg tagctctgct ggtggctgct     2220
gaattctggg aacaaggtga cctggagcgc acggtgctgc aacagaatcc cattcccatg     2280
atggacagaa acaaagcaga tgaactccct aagcttcaag tcggcttcat tgactttgtt     2340
tgcaccttcg tctacaagga attctcccgt ttccacgagg agatcacccc aatgttggac     2400
gggatcacca acaatcgcaa ggagtggaag gcgcttgctg atgagtacga tgccaagatg     2460
aaggtgcagg aggagaagaa gcagaaacag cagtcggcca agtcagcagc cgcaggaaat     2520
cagccggggg gaaaccccag cccaggggggt gcaactacat ccaagtcctg ctgcatccag     2580
t                                                                    2581
```

<210> SEQ ID NO 3
<211> LENGTH: 860
<212> TYPE: PRT
<213> ORGANISM: Artificial Sequence
<220> FEATURE:
<223> OTHER INFORMATION: hPDE6A amino acid sequence

<400> SEQUENCE: 3

```
Met Gly Glu Val Thr Ala Glu Glu Val Glu Lys Phe Leu Asp Ser Asn
1               5                   10                  15

Ile Gly Phe Ala Lys Gln Tyr Tyr Asn Leu His Tyr Arg Ala Lys Leu
            20                  25                  30

Ile Ser Asp Leu Leu Gly Ala Lys Glu Ala Ala Val Asp Phe Ser Asn
        35                  40                  45
```

-continued

```
Tyr His Ser Pro Ser Ser Met Glu Glu Ser Glu Ile Ile Phe Asp Leu
     50                  55                  60

Leu Arg Asp Phe Gln Glu Asn Leu Gln Thr Glu Lys Cys Ile Phe Asn
 65                  70                  75                  80

Val Met Lys Lys Leu Cys Phe Leu Leu Gln Ala Asp Arg Met Ser Leu
                 85                  90                  95

Phe Met Tyr Arg Thr Arg Asn Gly Ile Ala Glu Leu Ala Thr Arg Leu
            100                 105                 110

Phe Asn Val His Lys Asp Ala Val Leu Glu Asp Cys Leu Val Met Pro
             115                 120                 125

Asp Gln Glu Ile Val Phe Pro Leu Asp Met Gly Ile Val Gly His Val
        130                 135                 140

Ala His Ser Lys Lys Ile Ala Asn Val Pro Asn Thr Glu Glu Asp Glu
145                 150                 155                 160

His Phe Cys Asp Phe Val Asp Ile Leu Thr Glu Tyr Lys Thr Lys Asn
                165                 170                 175

Ile Leu Ala Ser Pro Ile Met Asn Gly Lys Asp Val Val Ala Ile Ile
            180                 185                 190

Met Ala Val Asn Lys Val Asp Gly Ser His Phe Thr Lys Arg Asp Glu
        195                 200                 205

Glu Ile Leu Leu Lys Tyr Leu Asn Phe Ala Asn Leu Ile Met Lys Val
210                 215                 220

Tyr His Leu Ser Tyr Leu His Asn Cys Glu Thr Arg Arg Gly Gln Ile
225                 230                 235                 240

Leu Leu Trp Ser Gly Ser Lys Val Phe Glu Glu Leu Thr Asp Ile Glu
                245                 250                 255

Arg Gln Phe His Lys Ala Leu Tyr Thr Val Arg Ala Phe Leu Asn Cys
            260                 265                 270

Asp Arg Tyr Ser Val Gly Leu Leu Asp Met Thr Lys Gln Lys Glu Phe
        275                 280                 285

Phe Asp Val Trp Pro Val Leu Met Gly Glu Val Pro Pro Tyr Ser Gly
    290                 295                 300

Pro Arg Thr Pro Asp Gly Arg Glu Ile Asn Phe Tyr Lys Val Ile Asp
305                 310                 315                 320

Tyr Ile Leu His Gly Lys Glu Asp Ile Lys Val Ile Pro Asn Pro Pro
                325                 330                 335

Pro Asp His Trp Ala Leu Val Ser Gly Leu Pro Ala Tyr Val Ala Gln
            340                 345                 350

Asn Gly Leu Ile Cys Asn Ile Met Asn Ala Pro Ala Glu Asp Phe Phe
        355                 360                 365

Ala Phe Gln Lys Glu Pro Leu Asp Glu Ser Gly Trp Met Ile Lys Asn
    370                 375                 380

Val Leu Ser Met Pro Ile Val Asn Lys Lys Glu Glu Ile Val Gly Val
385                 390                 395                 400

Ala Thr Phe Tyr Asn Arg Lys Asp Gly Lys Pro Phe Asp Glu Met Asp
                405                 410                 415

Glu Thr Leu Met Glu Ser Leu Thr Gln Phe Leu Gly Trp Ser Val Leu
            420                 425                 430

Asn Pro Asp Thr Tyr Glu Ser Met Asn Lys Leu Glu Asn Arg Lys Asp
        435                 440                 445

Ile Phe Gln Asp Ile Val Lys Tyr His Val Lys Cys Asp Asn Glu Glu
    450                 455                 460
```

-continued

Ile Gln Lys Ile Leu Lys Thr Arg Glu Val Tyr Gly Lys Glu Pro Trp
465                 470                 475                 480

Glu Cys Glu Glu Glu Leu Ala Glu Ile Leu Gln Ala Glu Leu Pro
            485                 490                 495

Asp Ala Asp Lys Tyr Glu Ile Asn Lys Phe His Phe Ser Asp Leu Pro
            500                 505                 510

Leu Thr Glu Leu Glu Leu Val Lys Cys Gly Ile Gln Met Tyr Tyr Glu
            515                 520                 525

Leu Lys Val Val Asp Lys Phe His Ile Pro Gln Glu Ala Leu Val Arg
            530                 535                 540

Phe Met Tyr Ser Leu Ser Lys Gly Tyr Arg Lys Ile Thr Tyr His Asn
545                 550                 555                 560

Trp Arg His Gly Phe Asn Val Gly Gln Thr Met Phe Ser Leu Leu Val
                565                 570                 575

Thr Gly Lys Leu Lys Arg Tyr Phe Thr Asp Leu Glu Ala Leu Ala Met
                580                 585                 590

Val Thr Ala Ala Phe Cys His Asp Ile Asp His Arg Gly Thr Asn Asn
            595                 600                 605

Leu Tyr Gln Met Lys Ser Gln Asn Pro Leu Ala Lys Leu His Gly Ser
            610                 615                 620

Ser Ile Leu Glu Arg His His Leu Glu Phe Gly Lys Thr Leu Leu Arg
625                 630                 635                 640

Asp Glu Ser Leu Asn Ile Phe Gln Asn Leu Asn Arg Arg Gln His Glu
                645                 650                 655

His Ala Ile His Met Met Asp Ile Ala Ile Ala Thr Asp Leu Ala
            660                 665                 670

Leu Tyr Phe Lys Lys Arg Thr Met Phe Gln Lys Ile Val Asp Gln Ser
            675                 680                 685

Lys Thr Tyr Glu Ser Glu Gln Glu Trp Thr Gln Tyr Met Met Leu Glu
            690                 695                 700

Gln Thr Arg Lys Glu Ile Val Met Ala Met Met Thr Ala Cys Asp
705                 710                 715                 720

Leu Ser Ala Ile Thr Lys Pro Trp Glu Val Gln Ser Gln Val Ala Leu
                725                 730                 735

Leu Val Ala Ala Glu Phe Trp Glu Gln Gly Asp Leu Glu Arg Thr Val
            740                 745                 750

Leu Gln Gln Asn Pro Ile Pro Met Met Asp Arg Asn Lys Ala Asp Glu
            755                 760                 765

Leu Pro Lys Leu Gln Val Gly Phe Ile Asp Phe Val Cys Thr Phe Val
770                 775                 780

Tyr Lys Glu Phe Ser Arg Phe His Glu Glu Ile Thr Pro Met Leu Asp
785                 790                 795                 800

Gly Ile Thr Asn Asn Arg Lys Glu Trp Lys Ala Leu Ala Asp Glu Tyr
                805                 810                 815

Asp Ala Lys Met Lys Val Gln Glu Glu Lys Gln Lys Gln Gln Ser
            820                 825                 830

Ala Lys Ser Ala Ala Ala Gly Asn Gln Pro Gly Gly Asn Pro Ser Pro
            835                 840                 845

Gly Gly Ala Thr Thr Ser Lys Ser Cys Cys Ile Gln
            850                 855                 860

<210> SEQ ID NO 4
<211> LENGTH: 543
<212> TYPE: DNA

<213> ORGANISM: Artificial Sequence
<220> FEATURE:
<223> OTHER INFORMATION: WPREm nucleotide sequence

<400> SEQUENCE: 4

```
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact  240
ggttggggca ttgccaccac ctgtcagctc ctttccggga cttttgcttt cccctccct    300
attgccacgg cggaactcat cgccgcctgc cttgcccgct gctggacagg ggctcggctg   360
ttgggcactg acaattccgt ggtgttgtcg gggaagctga cgtcctttcc agggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cga                                                                543
```

<210> SEQ ID NO 5
<211> LENGTH: 208
<212> TYPE: DNA
<213> ORGANISM: Artificial Sequence
<220> FEATURE:
<223> OTHER INFORMATION: BGH pA nucleotide sequence

<400> SEQUENCE: 5

```
ctgtgccttc tagttgccag ccatctgttg tttgcccctc cccgtgcct tccttgaccc     60
tggaaggtgc cactcccact gtcctttcct aataaaatga ggaaattgca tcgcattgtc   120
tgagtaggtg tcattctatt ctggggggtg ggtggggca ggacagcaag ggggaggatt    180
gggaagacaa tagcaggcat gctgggga                                     208
```

<210> SEQ ID NO 6
<211> LENGTH: 130
<212> TYPE: DNA
<213> ORGANISM: Artificial Sequence
<220> FEATURE:
<223> OTHER INFORMATION: L-ITR nucleotide sequence

<400> SEQUENCE: 6

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct                                                         130
```

<210> SEQ ID NO 7
<211> LENGTH: 130
<212> TYPE: DNA
<213> ORGANISM: Artificial Sequence
<220> FEATURE:
<223> OTHER INFORMATION: R-ITR nucleotide sequence

<400> SEQUENCE: 7

```
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgcag                                                         130
```

<210> SEQ ID NO 8
<211> LENGTH: 5591

```
<212> TYPE: DNA
<213> ORGANISM: Artificial Sequence
<220> FEATURE:
<223> OTHER INFORMATION: pGL2.KanR vector backbone nucleotide sequence

<400> SEQUENCE: 8
tgggcctcag tgagcgagcg agcgcgcagc tgcattaatg aatcggccaa cgcgcgggga      60
gaggcggttt gcgtattggg cgctcttccg cttcctcgct cactgactcg ctgcgctcgg     120
tcgttcggct gcggcgagcg gtatcagctc actcaaaggc ggtaatacgg ttatccacag     180
aatcagggga taacgcagga agaacatgt cgcgttgctg gcgttttttcc ataggctccg     240 ccccctgac gagcatcaca aaatcgacg ctcaagtcag aggtggcgaa acccgacagg     300
actataaaga taccaggcgt ttccccctgg aagctccctc gtgcgctctc ctgttccgac     360
cctgccgctt accggatacc tgtccgcctt tctcccttcg ggaagcgtgg cgctttctca     420
tagctcacgc tgtaggtatc tcagttcggt gtaggtcgtt cgctccaagc tgggctgtgt     480
gcacgaaccc cccgttcagc ccgaccgctg cgccttatcc ggtaactatc gtcttgagtc     540
caacccggta agacacgact tatcgccact ggcagcagcc actggtaaca ggattagcag     600
agcgaggtat gtaggcggtg ctacagagtt cttgaagtgg tggcctaact acggctacac     660
tagaagaaca gtatttggta tctgcgctct gctgaagcca gttaccttcg gaaaaagagt     720
tggtagctct tgatccggca acaaaccac cgctggtagc ggtggttttt ttgtttgcaa     780
gcagcagatt acgcgcagaa aaaaggatc tcaagaagat cctttgatct tttctacggg     840
gtctgacgct cagtggaacg aaaactcacg ttaagggatt ttggtcatga ctgtggaatg     900
tgtgtcagtt aggcgacata ggtgatctat gtagaagcct agtggaacag ttagtttga     960 gtagctttag aatgtaaatt ctgggatcat agtgtagtaa tctctaatta acggtgacgg    1020
tttgtaagac aggtcttcgc aaaatcaagc ggcaggtgat ttcaacagat tcttgctgat    1080
ggtttaggcg tacaatgccc tgaagaataa gtaagagaat agcactcctc gtcgcctaga    1140
attacctacc ggcgtccacc ataccttcga ttatcgcgcc cactctccca ttagtcggca    1200
caggtggatg tgttgcgata gcccgctaag atattctaag gcgtaacgca gatgaatatt    1260
ctacagagtt gccataggcg ttgaacgctt cacggacgat aggaatgttg cgtatagagc    1320
gtgagtcatc gaagtggtgt atacactcgt acttaacatc tagcccggct ctatcagtac    1380
accagtgcct tgaatgacat actcatcatt aaactttctc aacagtcaaa cgaccaagtg    1440
catttccaag gagtgcgaag gagattcatt ctctcgccag cactgtaata ggcactaaaa    1500
gagtgaagat aagctagagt gccgtgctaa gacggtgtcg gaacaaagcg gtcttacggt    1560
cagtcgtatt tcctgtcgag tcccgtccag ttgagcgtat cactcccagt gtactagcaa    1620
gccgagaagg ctgtgcttgg agtcaatcgg atgtaggatg gtctccagac accgggccac    1680
cactcttcac gcctagaagc atagaacgtc gagcagacat caaagtctta gtaccggacg    1740
tgccgtttca ctgcgaatat tacctgaagc tgtaccgtta ttgcggagca aagtgacagt    1800
gctgctctta tcatatttgt attgacgaca gccgccttcg cggtttcctc agactctaga    1860
tcgaatacag gcttattgta ggcagaggca cgcccttgtt agtggctgcg gcaatatctt    1920
ccgatcccct tgtctaacca tgaatcaatt ctctcatttg aagaccctaa tatgtcatca    1980
ttagtgtttc aaatgccacc aaataccgcc tagaaatgtc tatgatgtgt gtccactaga    2040
agttgattca caaacgactg ctagaatcgc gtgataggc atcttgaagt ttacattgtt    2100
gtatcgcaag gtactccgat cttaatggat gcgaagtggt acgatgcaa tcaagcgcgt    2160
```

```
gagagcggta cattagagcg ttcacctacg ctacgctaac gggcgattct gataagaatg    2220
cacattgcgt cgattcataa gatgtctcga ccgcatgcgc aacttgtgaa gtgtctacta    2280
tccctaagcg catatctcgc acagtaaccg aatatgtcgg catctgatgt taccgttgag    2340
ttagtgttca gctcacggaa cttattgtat gagtagagat ttgtaagagc tgttagttag    2400
ctcgctcagc taatagttgc ccacacaacg tcaaattaga gaacggtcgt aacattatcg    2460
gtggttctct aactactatc agtacccacg actcgactct gccgcagcta ggtatcgcct    2520
gaaagccagt cagcgttaag gagtgctctg accaggacaa caggcgtagt gagagttact    2580
tgttcgttgc tcttccgact cggacctgag ttcgccaacg acccacttga ggtctgagcc    2640
ggtgaagaga agtaagcatc tcgttcgcag cttgccagca ctttcagaac atgaccccta    2700
tttgtttatt tttctaaata cattcaaata tgtatccgct catgagacaa taaccctgat    2760
aaatgcttca ataatattga aaaggaaga gtggccgcct cggcctaggc ttttgcaaag    2820
atcgatcaag agacaggatg aggatcgttt cgcatgattg aacaagatgg attgcacgca    2880
ggttctccgg ccgcttgggt ggagaggcta ttcggctatg actgggcaca acagacaatc    2940
ggctgctctg atgccgccgt gttccggctg tcagcgcagg ggcgcccggt tcttttgtc     3000 aagaccgacc tgtccggtgc cctgaatgaa ctgcaagacg aggcagcgcg gctatcgtgg    3060
ctggccacga cgggcgttcc ttgcgcagct gtgctcgacg ttgtcactga agcgggaagg    3120
gactggctgc tattgggcga agtgccgggg caggatctcc tgtcatctca ccttgctcct    3180
gccgagaaag tatccatcat ggctgatgca atgcggcggc tgcatacgct tgatccggct    3240
acctgcccat cgaccacca agcgaaacat cgcatcgagc gagcacgtac tcggatggaa    3300
gccggtcttg tcgatcagga tgatctggac gaagagcatc aggggctcgc gccagccgaa    3360
ctgttcgcca ggctcaaggc gagcatgccc gacggcgagg atctcgtcgt gacccatggc    3420
gatgcctgct tgccgaatat catggtggaa aatggccgct tttctggatt catcgactgt    3480
ggccggctgg gtgtggcgga ccgctatcag gacatagcgt tggctacccg tgatattgct    3540
gaagagcttg gcggcgaatg ggctgaccgc ttcctcgtgc tttacggtat cgccgctccc    3600
gattcgcagc gcatcgcctt ctatcgcctt cttgacgagt tcttctgagg taccatgatg    3660
cgtgcatggt agaatgactc ttgataacgg acttcgacta ggcaatatcc cttgtcaact    3720
tgtcgaggag aaaagtattg actgaagcgc tcccggcaca acggccaaag aagtctcagc    3780
aatgttctta tttccgaatg acatgcgtct ccttgcgggt aaatcgccga ccgcaaaact    3840
taggagccag gatacagata ggtctaactt aggttaaggg agtaaatcct gggatcgttc    3900
agttgtaacc atatacttac gctggggctt ctccggcgga tgttactgtc accaaccacg    3960
agatttgaag taaacgcatg attgagcaca tagccgcgct atccgacaat ctccaaattg    4020
ataacatacc gttccatgaa ggccagaatt acttaccggc cctttccatg cgtgcgccat    4080
accgcactct gcgcttatcc gtccgagggg agagtgtgcg atcctccgtt aagatattct    4140
cacgtatgac gtagctatgt attgtgcaga ggtagcgaag gcgttgaaca cttcacagat    4200
ggtggggatt cggcaaaggg gcgtgataac ttggggacta acataggcgt aaactacgat    4260
ggcaccaact caatcgcagc tcgtgcgccc tgaatcaacg tactcatctc aactgattct    4320
cggcaatcta cggagcgact tgattatcaa cacctgtcta gcagttctaa tcttctgcca    4380
acatcgtaca tagcctccaa gagattatca tacctatcgg cacagaagtg acacgacgcc    4440
gaagggtagc ggacttctgg tcaaccacaa ttccccaggg gacaggtcct gcggtgcgca    4500
tcactttgta agtgcaagca acccaagtga gcccagcctg gactgagctg gttcctgtgt    4560
```

```
caggtcgagg ctggggatga cagctcttgt aaacatagtg atcaagcgtg gcgtcgaacg    4620
gtcgagaaac tcatagtacc tcgggtagca acttactcag gttattgctt gaagctgtac    4680
tatttcagga gcgctgaagg tctcttcttc tgtagactga actcgcaagg gtcgtgaagt    4740
cggttccttc aatgcttaac aagaacaaag gcttactgtg cagactggaa cgcccatcta    4800
gcggctcgcg tcttgaatgc tcggtcccct ttgtcattgc ggatacaatc catttccctc    4860
attcaccagc ttgcgaagtc tacattgagt agacgaatgc gacctagaag aggtgcgctt    4920
cagaacttgt gaggagtggt tgatgctcta tactccattt ggtgtttcgt gcatcaccgc    4980
gataggctga caagaggtct tgaacattga atagcaaggc acttccggtc tcatagaaga    5040
gagcacggga taaggtacgc gcgtggtacg ggaggatcaa ggggctacac gatagaaagg    5100
cttctccctc actcgctagg aggcaaatgc agaacgctgg ttactactac gatacgtgaa    5160
acttgtccaa cggttgccca aagtgttaag tgtctatcac cctagtgccg tttcccggag    5220
aaaacgccag gttgaatccg catttgaagc tacgatggtg aagtctgggt cgagcgcgcc    5280
gcatgttgat tgcgtgagta ggctcgacca agaaccgcta gtagcgtcgc tgtagaaata    5340
gttctcgaca gaccgtcgag tttagaaaat ggtagcagca ttgttcgcat ctcaatcaag    5400
tatggattac ggtgtttaca ctgtcctgcg gctacccatc gcctgaaatc cagctcgtgt    5460
caagccattg cctctccggg acgccgcatg aagtaactac atataccttg cacgggttga    5520
ctgcggtccg ttcagactcg accaaggaca caatccagcg atcggtgcgg gcctcttcgc    5580
tattacgcca g                                                        5591
```